United States Patent
Ito et al.

(10) Patent No.: US 8,298,135 B2
(45) Date of Patent: *Oct. 30, 2012

(54) MEDICAL DEVICE WITH ENDOSCOPE AND INSERTABLE INSTRUMENT

(75) Inventors: Seiichi Ito, Hachioji (JP); Shunya Akimoto, Kawasaki (JP); Junichi Onishi, Hachioji (JP); Jun Hasegawa, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 493 days.

This patent is subject to a terminal disclaimer.

(21) Appl. No.: 12/469,111

(22) Filed: May 20, 2009

(65) Prior Publication Data

US 2009/0292166 A1    Nov. 26, 2009

(30) Foreign Application Priority Data

May 23, 2008    (JP) ................................. 2008-135634

(51) Int. Cl.
*A61B 1/00* (2006.01)
*A61B 1/06* (2006.01)

(52) U.S. Cl. .......................... 600/117; 600/103; 600/109

(58) Field of Classification Search .................. 600/109, 600/117–118, 156, 160, 182; 382/130, 151, 382/276, 294; 128/922
See application file for complete search history.

(56) References Cited

U.S. PATENT DOCUMENTS

| | | | |
|---|---|---|---|
| 5,331,947 A * | 7/1994 | Shturman | 600/115 |
| 5,704,897 A | 1/1998 | Truppe | |
| 5,776,050 A * | 7/1998 | Chen et al. | 600/117 |
| 6,773,393 B1 * | 8/2004 | Taniguchi et al. | 600/117 |
| 7,195,587 B2 * | 3/2007 | Taniguchi et al. | 600/117 |
| 7,901,348 B2 | 3/2011 | Soper et al. | |

(Continued)

FOREIGN PATENT DOCUMENTS

EP    1543765    6/2005

(Continued)

OTHER PUBLICATIONS

JP 2003265408 A- Machine Translation.*

(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

A medical device for examination or treatment based on a reference point A1, including: a virtual endoscopic image generation section configured to generate a virtual endoscopic image from a plurality of different sight line positions using three-dimensional image data of a bronchus that is obtained in advance; an image retrieving section configured to retrieve a virtual endoscopic image highly similar to a real image; a reference-point setting section configured to set the reference point A1 based on a line-of-sight position A0 of the highly similar virtual endoscopic image; a relative-position calculation section configured to calculate a relative position of a treatment instrument to the reference point A1; a movement detection section configured to detect a movement of the reference point A1 or the bronchus; and a position correction section configured to correct the relative position in response to the movement of the reference point A1 or the bronchus.

6 Claims, 20 Drawing Sheets

U.S. PATENT DOCUMENTS

| | | | |
|---|---|---|---|
| 7,940,967 B2 * | 5/2011 | Ozaki et al. | 382/128 |
| 7,951,070 B2 * | 5/2011 | Ozaki et al. | 600/118 |
| 2005/0033117 A1 | 2/2005 | Ozaki et al. | |
| 2005/0085718 A1 * | 4/2005 | Shahidi | 600/424 |
| 2005/0182295 A1 | 8/2005 | Soper et al. | |
| 2006/0149134 A1 * | 7/2006 | Soper et al. | 600/182 |
| 2007/0060792 A1 | 3/2007 | Draxinger et al. | |
| 2007/0293721 A1 | 12/2007 | Gilboa | |

FOREIGN PATENT DOCUMENTS

| | | |
|---|---|---|
| JP | 2000-135215 | 5/2000 |
| JP | 2002-119507 | 4/2002 |
| JP | 2003-265408 | 9/2003 |
| JP | 2003265408 A * | 9/2003 |
| JP | 2004-89484 | 3/2004 |
| JP | 2004-180940 | 7/2004 |
| JP | 2005-131042 | 5/2005 |
| WO | WO 2007/008289 A2 | 1/2007 |

OTHER PUBLICATIONS

U.S. Office Action dated Jan. 27, 2012 in related case U.S. Appl. No. 12/468,277.

Machine Translation of JP 2003-265408 (non translated version previously submitted in IDS dated Sep. 23, 2009).

Bricault et al., "Registration of Real and CT-Derived Virtual Bronchoscopic Images to Assist Transbronchial Biopsy", pp. 703-714, IEEE Transactions on Medical Imaging, vol. 17, No. 5, Oct. 1998, XP011035768.

U.S. Office Action dated Jul. 26, 2011 in related case U.S. Appl. No. 12/468,277.

U.S. Office Action dated Aug. 31, 2011 in related case U.S. Appl. No. 12/469,000.

Extended European Search Report dated Aug. 14, 2009 from related EP 09006687.9.

* cited by examiner

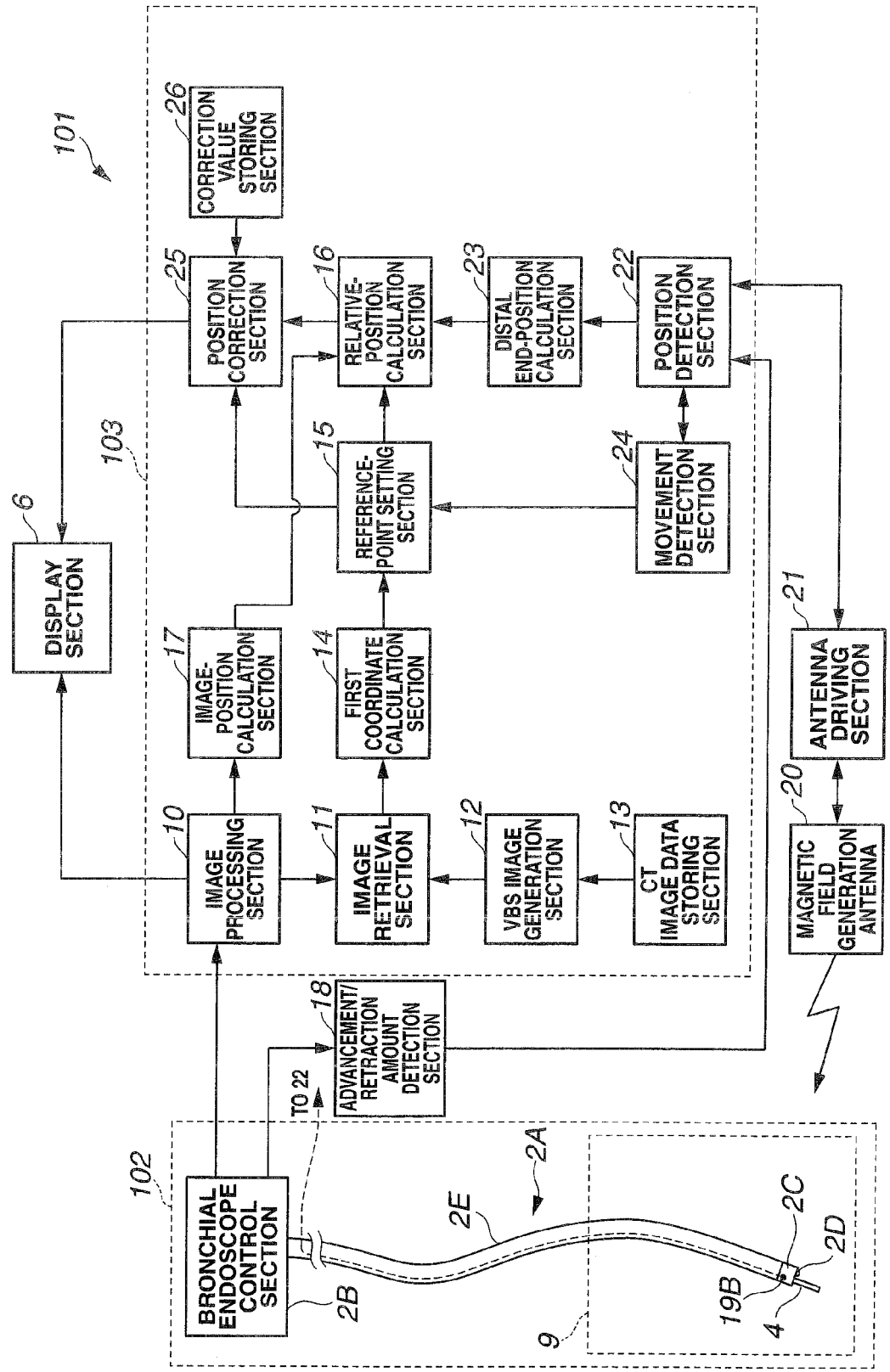

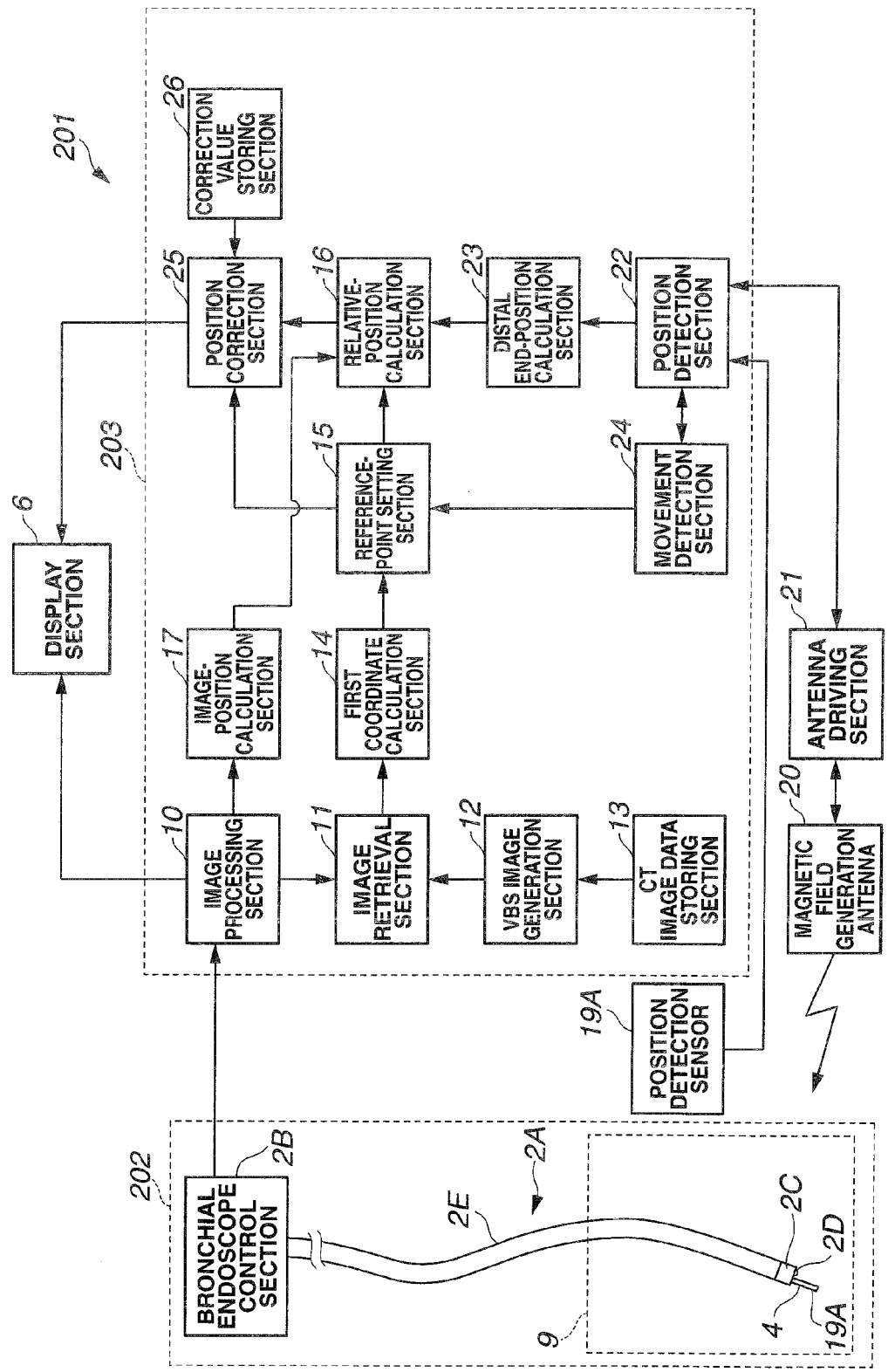

MEDICAL DEVICE WITH ENDOSCOPE AND INSERTABLE INSTRUMENT

This application claims benefit of Japanese Application No. 2008-135634 filed in Japan on May 23, 2008, the contents of which are incorporated by this reference.

BACKGROUND OF THE INVENTION

1. Field of the Invention

The present invention relates to a medical device having an image pickup section that is able to pick up images of a tube cavity in a subject, more particularly, to a medical device that performs examination or treatment with high accuracy using virtual endoscopic images of a tube cavity in body based on three-dimensional image data of a subject.

2. Description of the Related Art

In recent years, diagnoses have been widely made using three-dimensional images. For example, a diagnosis for a target site can be made using three-dimensional image data of a subject which is obtained by picking up tomographic images of the subject with an X-ray CT (Computed Tomography) apparatus.

In the CT apparatus, a subject is continuously moved while X-ray radiating positions and detection positions are continuously rotated for continuous helical scanning of the subject (helical scan). A large number of resulting continuous two-dimensional tomographic images of the subject are used to create a three-dimensional image.

A three-dimensional image of bronchus of lungs is one type of the three-dimensional images used in diagnoses. Such a three-dimensional image of bronchus is used in a three-dimensional detection of the position of a diseased area with suspected lung cancer for example. In order to check the diseased area by a biopsy, a bronchus endoscope is inserted into the subject and a biopsy needle or biopsy forceps are extended out from a distal end portion of the bronchus endoscope, so as to collect tissue samples of the target site.

In a tract such as bronchus in a body that is branched in multiple steps, in a case where a diseased area is located at the end of a bronchus, it is hard to bring the distal end of an insertion section of an endoscope to a position near the target site in a short period of time with accuracy. Thus, for example, Japanese Patent Application Laid-Open Publication No. 2004-180940 and Japanese Patent Application Laid-Open Publication No. 2005-131042 disclose navigation systems for insertion of endoscope in which a three-dimensional image of a tract in a subject is created based on image data of a three-dimensional area in the subject, and route along the tract to a target on the three-dimensional image is determined, so that virtual endoscopic images of the tract along the route can be created based on the image data.

SUMMARY OF THE INVENTION

A medical device of the present invention includes: an image pickup section that is able to pick up an image of a tube cavity in a subject; a medical instrument for examination or treatment in the tube cavity based on a reference point; a virtual endoscopic image generation section configured to generate a virtual endoscopic image in the tube cavity from a plurality of different line-of-sight positions based on three-dimensional image data of the tube cavity that is obtained in advance; an image retrieval section configured to retrieve the virtual endoscopic image highly similar to the endoscopic image of the tube cavity picked up by the image pickup section; a reference-point setting section configured to set the reference point based on the line-of-sight positions of the highly similar virtual endoscopic image; a relative-position calculation section configured to calculate a relative position of the medical instrument to the reference point; a movement detection section configured to detect a movement of the reference point or the subject; and a position correction section configured to correct the relative position in response to the movement of the reference point or the subject detected by the movement detection section.

BRIEF DESCRIPTION OF THE DRAWINGS

FIG. 9 is a configuration view showing a configuration of a medical device according to a modified example of the first embodiment;

FIG. 10 is a configuration view showing a configuration of a medical device according to a modified example of the first embodiment;

DETAILED DESCRIPTION OF THE PREFERRED EMBODIMENTS

First Embodiment

Now, with reference to the drawings, a medical device 1 of a first embodiment according to the present invention will be explained below.

Figure 1:
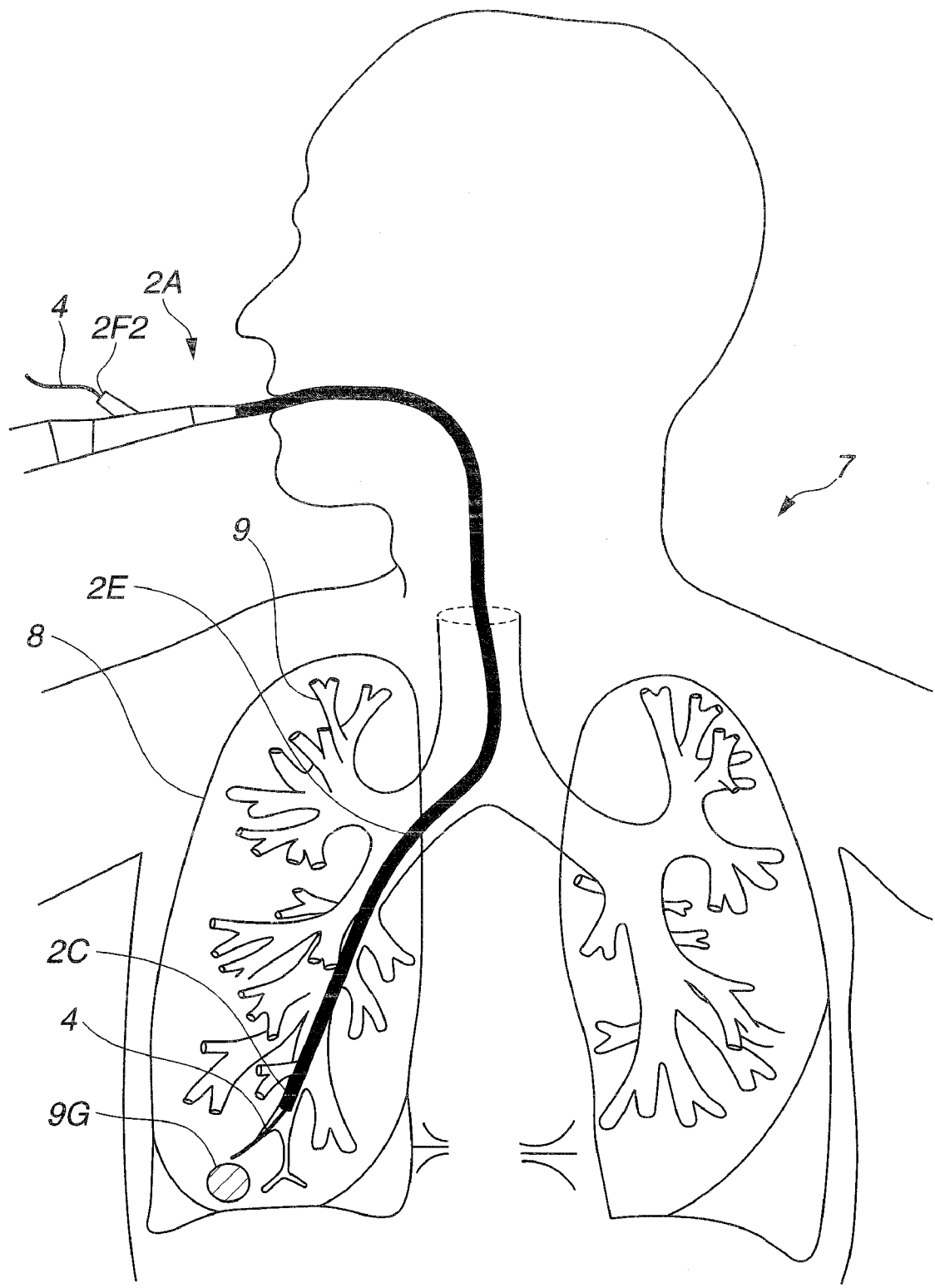
FIG. 1 is an illustrative view of a state where an examination or treatment of a target site at a bronchus in a test subject is being performed with a treatment instrument inserted through a channel of an endoscope.
Figure 2:
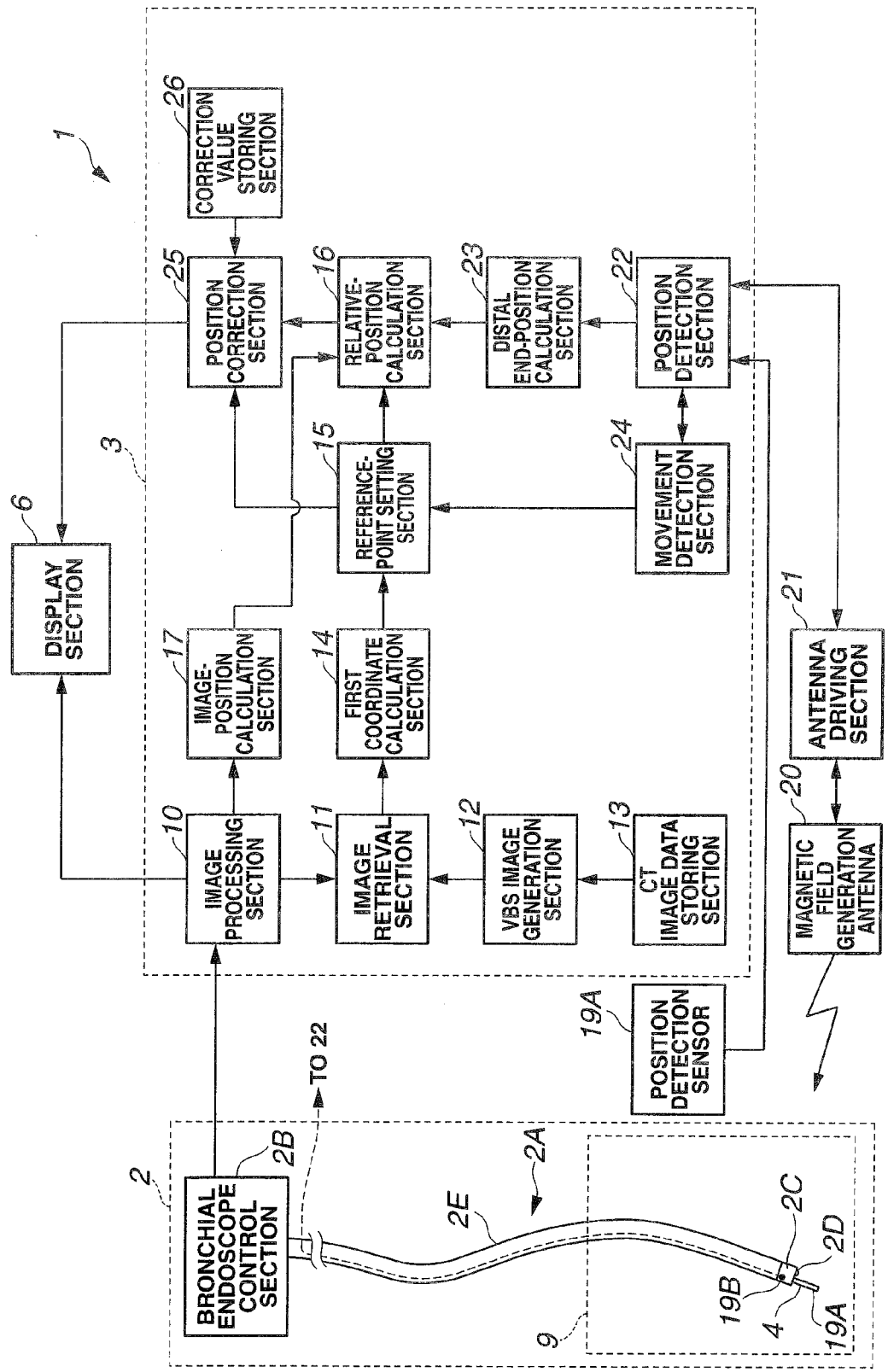
FIG. 2 is a configuration view showing a configuration of a medical device according to a first embodiment.

FIG. 1 is an illustrative view of a state where an examination or treatment of a target site at a bronchus in lungs of a patient is being performed with a medical instrument inserted through a channel of an endoscope, and FIG. 2 is a configuration view showing a configuration of the medical device 1 of the present embodiment.

FIG. 1 shows a state where a distal end portion 2C of an insertion section 2E of an endoscope 2A is inserted into a tract having the minimal diameter for insertion of the distal end portion 2C in bronchus 9. An elongated treatment instrument 4 that is a medical instrument inserted through the channel from a treatment instrument insertion port 2F2 is protruded out of the distal end portion 2C, and samples the tissues of the target site 9G.

As shown in FIG. 1, the insertion section 2E of the endoscope 2A is narrow so as to be insertable into narrow bronchus tube cavities, and has a diameter on the order of 3 mm for example, but the treatment instrument 4 has a diameter on the order of 1 mm for example, so as to be insertable into narrower end parts of the bronchus tube cavities. In many cases, the target site 9G at an end of a bronchus cannot be checked due to the narrowness by an image pickup section 2D arranged at the distal end portion 2C.

Next, as shown in FIG. 2, the medical device 1 of the present embodiment includes: an endoscope apparatus 2 configured to be inserted to the bronchus 9 that is a tube cavity in a body of the patient 7 who is the subject to pick up images of the inside of the bronchus 9 and to perform a biopsy of the target site 9G at the end of the bronchus (see FIG. 1); and the insertion assist apparatus 3.

The endoscope apparatus 2 is configured with an elongated insertion section 2E insertable through the bronchus 9 of the patient 7; an endoscope 2A having an image pickup section 2D such as a CCD arranged at the distal end portion 2C of the insertion section 2E; an endoscope control section 2B configured to control the endoscope 2A; a display section 6; and the like. The insertion section 2E has a channel (not shown) formed therein through which the treatment instrument 4 as a medical instrument can be inserted, and the distal end portion 2C is provided with a liquid-supply port 2G as an opening and a treatment instrument port 2F of the channel, thereby as shown in FIGS. 1 and 2, the treatment instrument 4 can be protruded from the treatment instrument port 2F.

As shown in FIG. 2, the insertion assist apparatus 3 includes: an image processing section 10; a CT image data storing section 13; a virtual endoscopic image (Virtual Bronchus Scope Image: hereinafter, also referred to as "VBS image") generation section 12 configured to generate a virtual endoscopic image; and an image retrieval section 11 configured to retrieve a virtual endoscopic image highly similar to an endoscopic image; a first coordinate calculation section 14; a reference-point setting section 15 configured to calculate a reference point based on a first coordinate point; an image-position calculation section 17; and a relative-position calculation section 16.

The image processing section 10 processes an endoscopic image (hereinafter, also referred to as "real image") picked up by the image pickup section 2D. The CT image data storing section 13 stores three-dimensional image data in a format such as DICOM (Digital Imaging and Communication in Medicine) that is generated in advance by a known CT apparatus (not shown) for picking up X-ray tomographic images of the patient 7. The VBS image generation section 12 generates a VBS image from the image data in DICOM format based on line-of-sight parameters which will be explained later. The image-position calculation section 17 calculates the position of the treatment instrument 4 based on a real image, and the relative-position calculation section 16 calculates the position of the treatment instrument 4 relative to a reference point based on the information from the image-position calculation section 17 and the reference-point setting section 15.

The insertion assist apparatus 3 may include a VBS image storing section (not shown) for storing VBS images generated by the VBS image generation section 12.

The insertion assist apparatus 3 further includes a movement detection section 24, a correction value storing section 26 configured to store correction values corresponding to positions in a tube cavity in advance, and a position detection section 22, the configuration of which will be explained below.

The insertion assist apparatus 3 assists the insertion of the treatment instrument 4 inserted through the channel 2F1 to the target site 9G of the bronchus 9 in the patient 7 after the distal end portion 2C is inserted to a position near the target site 9G at a tube cavity having the minimal diameter for insertion of the distal end portion 2C. The insertion assist apparatus 3 may be provided with a function of navigation system for insertion of the distal end portion 2C to a position near the target site 9G.

Figure 3:
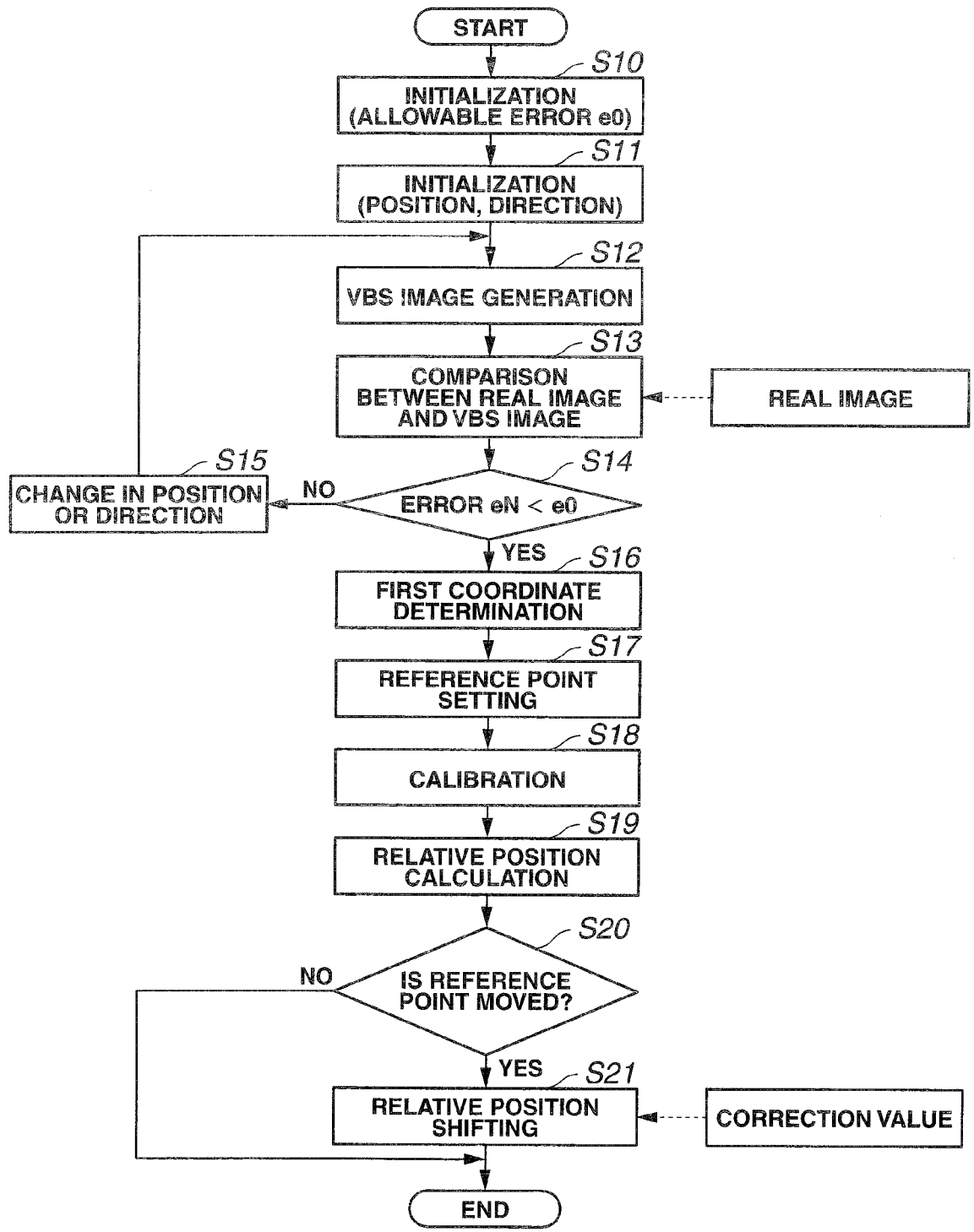
FIG. 3 is a flowchart illustrating a process flow of an insertion assist apparatus.

The insertion assist apparatus 3, first, retrieves a VBS image highly similar to a real image using the image retrieval section 11, and calculates the position (coordinate) and direction of the distal end portion 2C using the first coordinate calculation section 14. FIG. 3 is a flowchart illustrating a process flow of the insertion assist apparatus 3 for calculating the position and direction of the distal end portion 2C. Now, according to the flowchart of FIG. 3, the process flow for calculating the position and direction of the distal end portion 2C of the endoscope 2A by the insertion assist apparatus 3 will be explained below.

<Step S10>

First, an allowable error e0 is set for determination of similarity which is performed by the image retrieval section 11.

<Step S11>

The VBS image generation section 12 can generate a VBS image from a large number of different line-of-sight positions based on image data in DICOM format by changing six line-of-sight parameters. The parameters of a line-of-sight position as used herein are six-dimensional data including positions (x, y, z) and angles (θx, θy, θz).

<Step S12>

The VBS image generation section 12 generates one VBS image using three-dimensional image data of bronchus 9 of the patient 7 stored in the CT image data storing section 13, based on the initial values of the line-of-sight parameters.

Alternatively, the VBS image generation section 12 may generate virtual endoscopic images at branches of the bronchus in advance from a plurality of different line-of-sight positions, and store the images in a VBS image storing section (not shown), so that the image retrieval section 11 can retrieve a VBS image most highly similar to a real image from the stored VBS images, and set the line-of-sight parameters of the most highly similar VBS image as initial values at the line-of-sight position which are used at Step S11.

<Step S13>

The image retrieval section 11 compares the real image and the VBS image generated by the VBS image generation section 12 on the similarity to each other. The comparison between the images on the similarity is performed by a known image process which may be matching process on the level of pixel data or matching process on the level of features extracted from images. Because the matching process between the real image and the VBS image is performed for every frame of the real image, the actual comparison is made based on the similarity between the static endoscopic image and the virtual endoscopic image. The matching process need not be performed for all of the frames of the real image, but is repeated at appropriate intervals.

<Step S14 and Step S15>

When the error e calculated by the image retrieval section 11 for the similarity between the real image and the VBS image is larger than the allowable error e0 (No), at Step S15, the image retrieval section 11 outputs line-of-sight parameter values of a slightly different position to the VBS image generation section 12. Then, at Step S12, the VBS image generation section 12 generates a next VBS image according to the new line-of-sight parameter set at Step S15.

The insertion assist apparatus 3 repeats the above loop processings, that is, outputs a different line-of-sight parameters, and as a result of that the VBS image generated by the VBS image generation section 12 is gradually changed to an image similar to the real image, and the error e between the images becomes equal to the allowable error e0 or less (Yes) after the loop processings are repeated several times.

<Step S16>

When the similarity error e between the VBS image and the real image becomes equal to the allowable error e0 or less, the first coordinate calculation section 14 calculates the position and direction of the distal end portion 2C using the line-of-sight parameters of the VBS image having higher similarity.

Figure 4A:
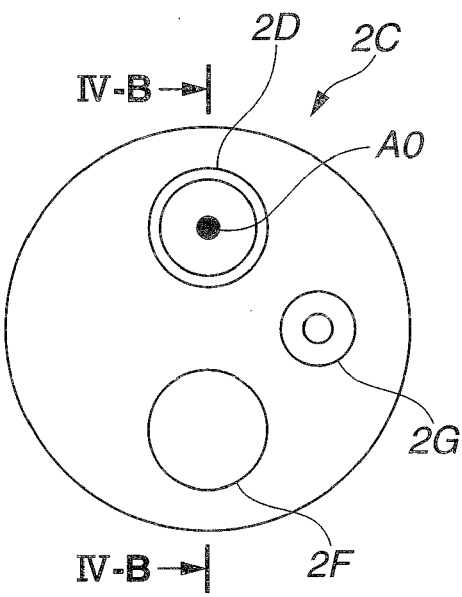
FIG. 4A is a schematic front view illustrating a configuration of a distal end portion.
Figure 4B:
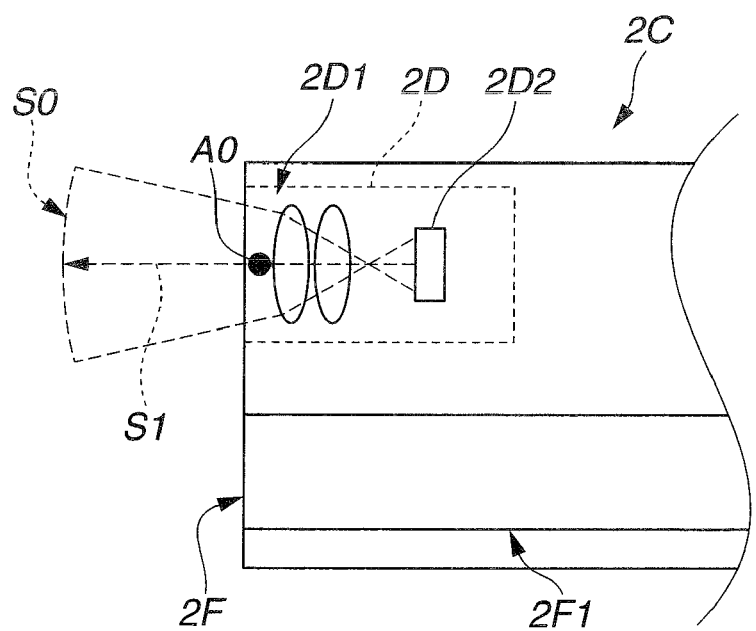
FIG. 4B is a schematic cross-sectional view taken along the IV-B-IV-B line of FIG. 4A.

Now, the structure of the distal end portion 2C will be explained below in more detail with FIG. 4A, FIG. 4B and FIG. 5. FIG. 4A is a schematic front view illustrating the configuration of the distal end portion 2C; FIG. 4B is a schematic cross-sectional view taken along the IV-B-IV-B line of FIG. 4A; and FIG. 5 is a schematic perspective view of the distal end portion 2C.

Figure 5:
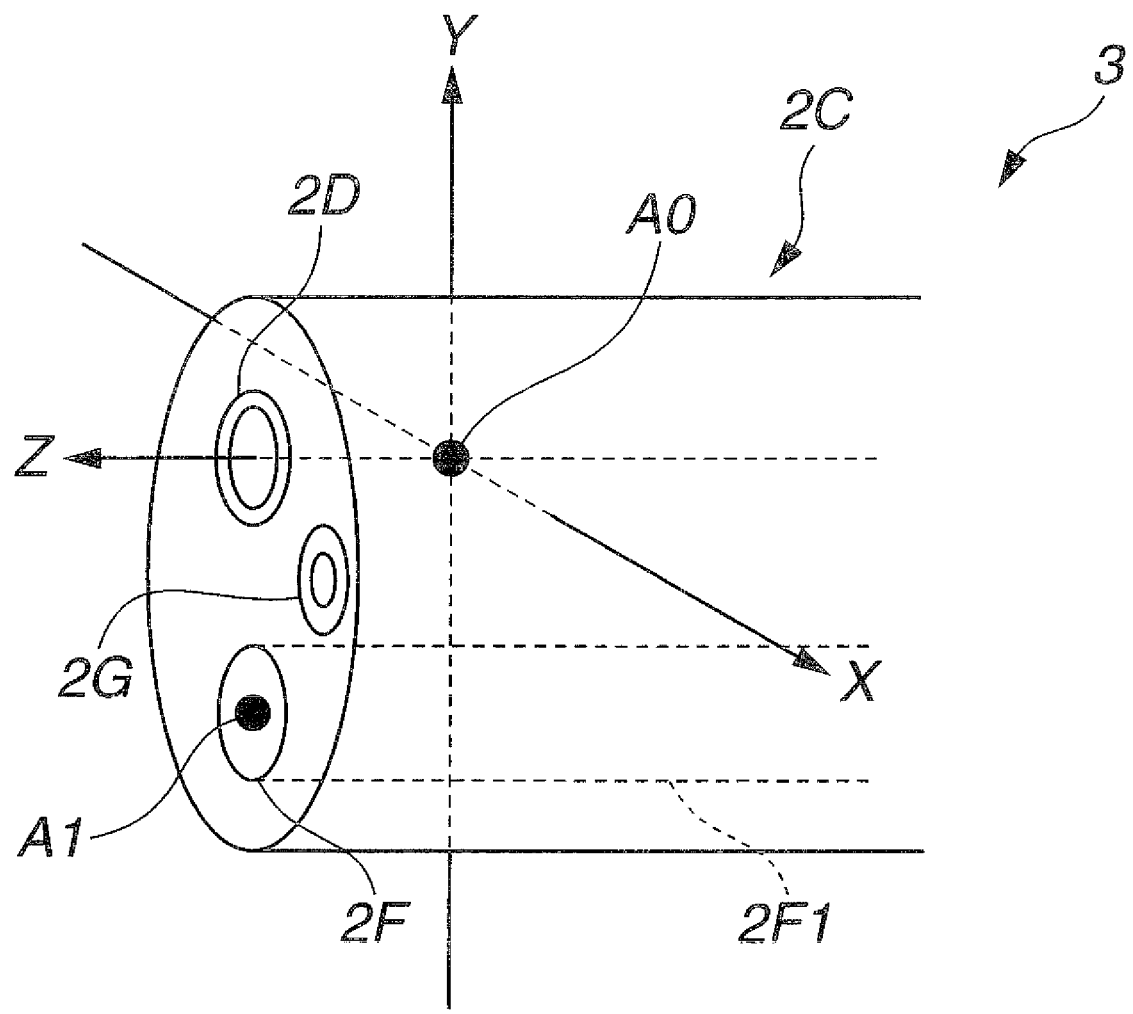
FIG. 5 is a schematic perspective view illustrating a distal end portion.

As shown in FIG. 4A, FIG. 4B and FIG. 5, the distal end portion 2C is provided with the treatment instrument port 2F of the channel 2F1, the image pickup section 2D, and the liquid-supply port 2G. The distal end portion 2C is further provided with an illumination section for illuminating the inside of tube cavity (not shown). The image pickup section 2D has an image pickup device 2D2 therein at the focus position of an optical system 2D1 to pick up an image within a field of view S0 in the direction with a line-of-sight S1 as a center.

The point on endoscope that corresponds to line-of-sight parameters of a VBS image represented by a first coordinate point calculated by the first coordinate calculation section 14 constitutes a pupil position A0 and the direction of the line-of-sight S1 as often called in an optical system.

Here, the coordinate of the first coordinate point A0 is expressed in a coordinate system of the virtual endoscopic image, in other words, a CT coordinate system, which means a lot to the medical device 1. That is, as already explained above, because the target site 9G for a biopsy is located at a bronchus end which the distal end portion 2C cannot reach, a surgeon cannot perform a biopsy and the like using the treatment instrument 4 while checking real images for the target site 9G. Therefore, a surgeon performs a biopsy based on the position of the target site 9G shown in a CT coordinate system in the three-dimensional image data that is obtained by CT in advance. However, the position of the distal end portion 2C, in other words, the position of the treatment instrument 4 for the biopsy protruded from the distal end portion 2C can be checked only in an endoscope coordinate system based on the distal end portion 2C which has no relationship with the CT coordinate system.

To the contrary, in the insertion assist apparatus 3, the coordinate of the target site 9G and the coordinate of the first coordinate point A0 on a part of the distal end portion 2C that is close to the target site 9G are expressed in the same CT coordinate system, which allows the surgeon to use the coordinate to bring the treatment instrument 4 to the target site 9G for a biopsy and the like. The examination or treatment performed using the medical device 1 herein may be spray of medication, biopsy, mucus sampling, extraction of foreign object, high-frequency cauterization, or the like.

The endoscope coordinate system for the medical device 1 shown in FIG. 5 is not the same with the CT coordinate system, but is a coordinate system which is processed to correspond to the CT coordinate system by the insertion assist apparatus 3, in other words, a coordinate system which can be transformed into the CT coordinate system by a coordinate transformation process.

<Step S17>

In the insertion assist apparatus 3, the reference-point setting section 15 sets a predetermined position (coordinate) at the distal end portion 2C as a reference point A1 based on the first coordinate point A0.

FIG. 5 shows an example in which the reference point A1 is set in the treatment instrument port 2F, more specifically at the center of the treatment instrument port 2F. That is, the reference point A1 is set in the treatment instrument port 2F serving as starting point from which the treatment instrument 4 is protruded. The relationship between the first coordinate point A0 and the center position A1 of the treatment instrument port 2F is known from the structure of the distal end portion 2C.

As described above, the reference point A1 is a predetermined position at a part near the image pickup section 2D close to the target site 9G. The part near the image pickup section 2D is in the bronchus that is a tube cavity in a body of the patient 7 who is the subject, and includes the inside of the image pickup section 2D. The position near the image pickup section 2D is preferably in the bronchus between the position A0 on the line-of-sight of the image pickup section 2D and the target site 9G, more preferably a predetermined position on the distal end portion 2C.

<Step S18>

Figure 6A:
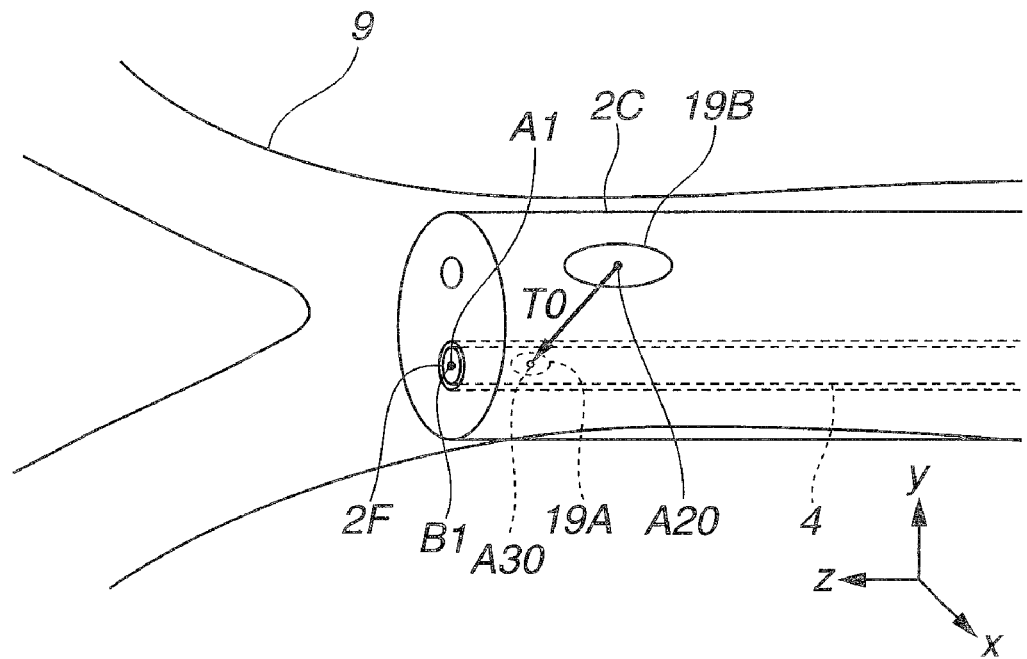
FIG. 6A is an illustrative view of a method for calculating the position of a distal end portion of a treatment instrument.
Figure 6B:
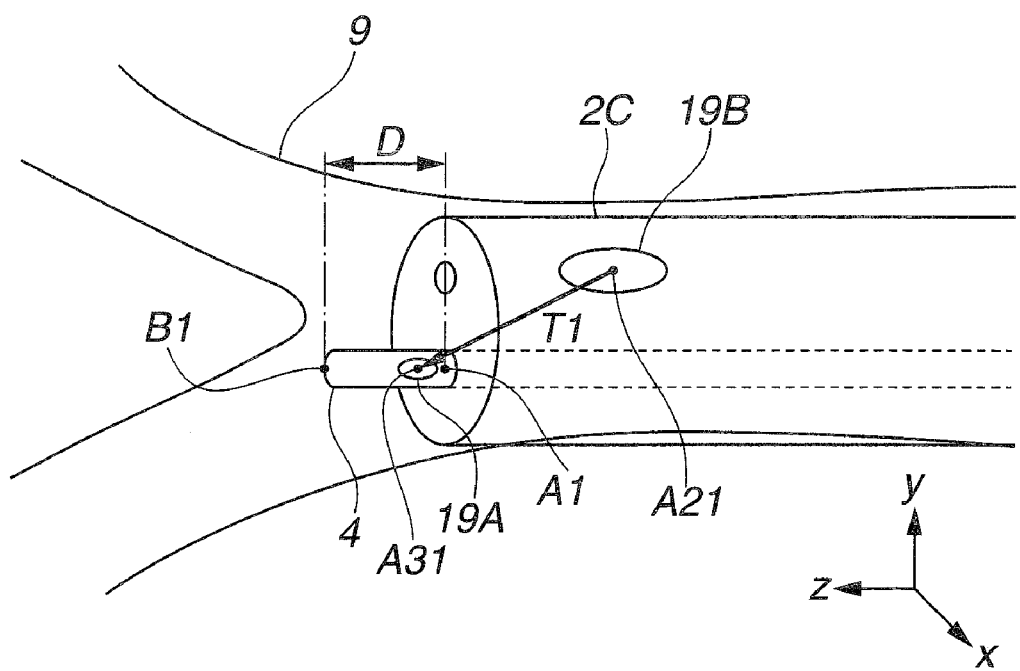
FIG. 6B is an illustrative view of a method for calculating the position of a distal end portion of a treatment instrument.

As shown in FIG. 2, FIG. 6A and FIG. 6B, the medical device 1 includes: a position detection sensor 19A arranged at a predetermined position of the treatment instrument 4; a position detection sensor 19B arranged at a predetermined position of the insertion section 2E; a magnetic field generation antenna 20; an antenna driving section 21; a position detection section 22; a distal end-position calculation section 23; and a movement detection section 24. The medical device 1 has a configuration with the above components which will be explained in detail later, so as to detect a position of the first position detection sensor 19A and a position of the second position detection sensor 19B. The medical device 1, first, calibrates the first position detection sensor 19A and the second position detection sensor 19B.

That is, as shown in FIG. 6A, a calibration is performed in a state where the treatment instrument 4 inserted through the channel 2F1 from the treatment instrument insertion port 2F2 on the proximal end side of the insertion section 2E is aligned to the reference point A1 at the distal end portion B1 thereof.

In the calibration, with the second position detection sensor 19B being at the position A20, and the first position detection sensor 19A being at the position A30 in the state shown in FIG. 6A, a transformation vector T0 of the position A30 based on the position A20 is calculated by the position detection section 22 according to the equation: "T0=A30−A20."
<Step S19>

Next, as shown in FIG. 6B, the treatment instrument 4 is operated to be protruded from the treatment instrument port 2F of the distal end portion 2C. At this time, with the second position detection sensor 19B being at the position A21, and the first position detection sensor 19A being at the position A31, a transformation vector T1 based on the position A21 is calculated by the position detection section 22 according to the equation: "T1=A31−A21." Then, the amount of protrusion D of the treatment instrument 4 from the treatment instrument insertion port 2F2 is calculated according to the equation: "D=T1−T0."

Because the second position detection sensor 19B is incorporated in the endoscope 2A, when the reference point A1 is located on the endoscope 2A, the relative relationship between the reference point A1 and the position A2 does not change and can be easily calculated. That is, the reference point A1 is associated with the position A2 with a transformation vector T12 according to the equation: "T12=A1−A2." Thus, based on the information from the distal end-position calculation section 23 and the reference-point setting section 15, on the assumption that the treatment instrument 4 is inserted in the direction along the centerline, as will be explained later, the relative-position calculation section 16 is able to calculate the position from the reference point A1 by the protruded amount D on the centerline as a treatment instrument distal end position B1.
<Step S20>

Figure 7A:
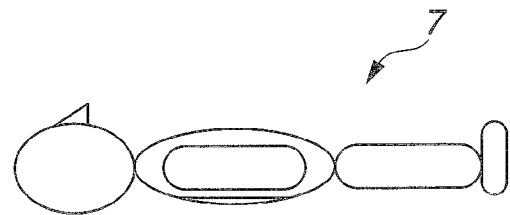
FIGS. 7A to 7D are schematic views illustrating states of a lung of a patient.
Figure 7B:
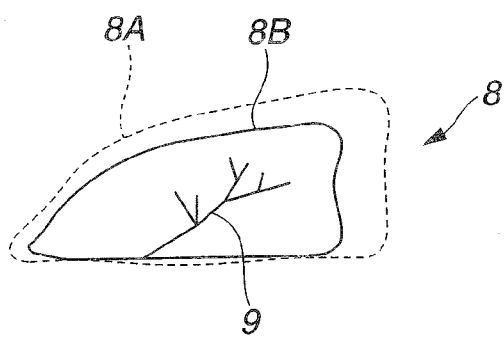
Figure 7C:
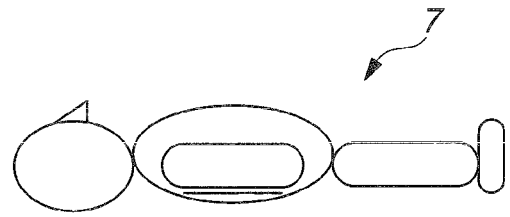
Figure 7D:
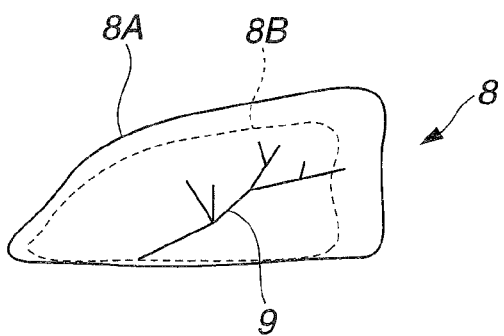

Next, a position correction will be explained below. FIGS. 7A to 7D are schematic views illustrating states of a lung 8 of the patient 7: FIGS. 7A and 7C are schematic side views of the patient 7; and FIGS. 7B and 7D are schematic views of a lung. FIGS. 7A and 7B show the patient and the lung during expiration; and FIGS. 7C and 7D show the patient and the lung during inspiration. As shown in FIGS. 7A to 7D, the shape and size of the lung of the patient 7 change as the patient 7 breathes. That is, the lung 8B during expiration shown in FIGS. 7A and 7B is smaller, and the lung 8A during inspiration shown in FIGS. 7C and 7D is larger.

In many cases, the patient 7 is in a state of inspiration while an image of the patient 7 is picked up by a CT apparatus, but in any case, the image is three-dimensional image data at an instant of the lung 8 the shape of which changes by breathing.

As a result, the shape of the bronchus 9 of the patient 7 under examination with the endoscope 2A being inserted in the patient 7 often does not match the three-dimensional image data of the patient 7 that is picked up by a CT apparatus in advance. Therefore, the medical device 1 includes a position correction section 25 configured to achieve the matching between the shape of the bronchus 9 of the patient 7 under examination and the three-dimensional image data of the patient 7 picked up by a CT apparatus.

There are two types of the correction method by the position correction section 25: a method for changing the shape in the three-dimensional image data of the bronchus 9 to be matched with the shape of the bronchus 9 under examination; and a method for changing the shape of the bronchus 9 under examination to be matched with the shape in the three-dimensional image data of the bronchus 9.

The medical device 1 of the present embodiment uses the latter method, because the three-dimensional image data has a large volume, and the correction of the data overloads the system. So, the medical device 1 changes an endoscope coordinate system, instead of changing a CT coordinate system, the results of which are the same.

As shown in FIG. 2 and FIG. 6A for example, the medical device 1 having the position detection sensor 19B at a predetermined position on the insertion section 2E is able to detect the movement of the position of the insertion section 2E, in other words, the movement of the reference point A1.

In the medical device 1, the position detection sensor 19B is a magnetic field detection sensor, and detects the position of the insertion section 2E by detecting the magnetic field from a plurality of magnetic field generation antennas placed outside of the patient 7. The magnetic field detection sensor may be MR sensor, hall element, or coil. The position detection sensor is not limited to a magnetic field detection sensor, but may be a position detection sensor such as an optical strain sensor and strain gauge.

The antenna driving section 21 causes the plurality of magnetic field generation antennas 20 (not shown) to generate alternating magnetic fields having different frequencies. The position detection sensor 19B distinguishes and detects each of the plurality of alternating magnetic fields having different frequencies, thereby the position detection section 22 can calculate the direction of each magnetic field generation antenna 20, which is used to detect the relative position of the position detection sensor 19B to the magnetic field generation antenna 20. Because the position of the position detection sensor 19B in the insertion section 2E is known, the medical device 1 is able to calculate the position of the reference point A1. The movement detection section 24 is able to detect the movement of the reference point A1 by the positional calculation in real time or as needed.

Figure 8A:
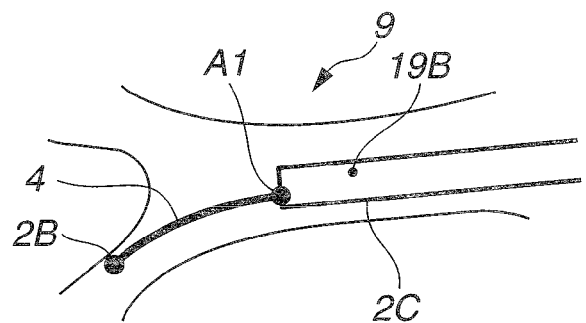
FIGS. 8A to 8C are illustrative views of a correction of a relative position based on a movement of a reference point.
Figure 8B:
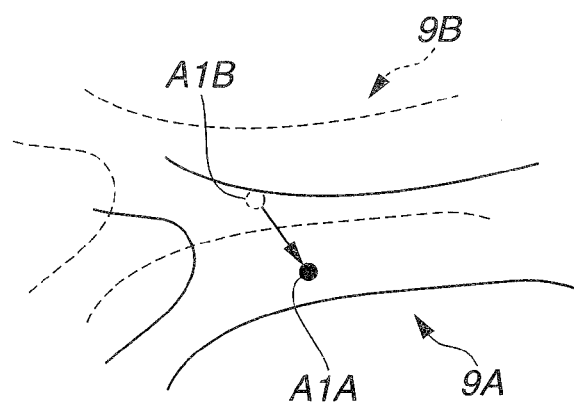
Figure 8C:
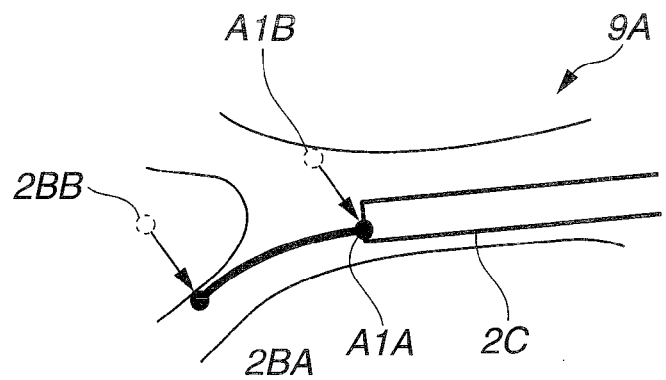

Now, with FIGS. 8A to 8C, a correction of relative position to a movement of the reference point A1 performed by the position correction section 25 will be explained below. FIGS. 8A to 8C are illustrative views of a correction of a relative position based on a movement of the reference point A1.

FIG. 8A shows a state where the treatment instrument 4 is protruded from the distal end portion 2C of the endoscope 2A that is inserted in the bronchus 9. The distal end portion 2C has a position detection sensor 19B arranged thereon.

As shown in FIG. 8B, when the position detection sensor 19B detects that the reference point has moved to a new position A1A from the position A1B (Yes), in the medical device 1, at the next step, the position correction section 25 performs a new correction of the position of the treatment instrument 4 based on the new reference point at the new position after the movement. Without any movement of the reference point A1, which means when the moved distance of the reference point A1 is smaller than a predetermined value (No), no correction is performed.
<Step S21>

As shown in FIG. 8C, in the medical device 1, the correction of the position of the distal end portion 2C by the position correction section 25 involves a translation of the position 2BB of the distal end portion 2C to the position 2BA by the movement amount in the direction of the movement of the reference point A1. That is, the relative-position calculation section 16 calculates a relative position using the position of the treatment instrument 4 that is a medical instrument and the new reference point obtained by the movement amount of the reference point A1.

In this case, because a protruded amount D of the treatment instrument 4 is not so large, the movement amount of the reference point A1 is considered to be equal to the movement amount of the treatment instrument 4 to simplify the process, which allows the medical device 1 to achieve a high-speed process. The position correction section 25 may appropriately change the amount of a correction based on information such as a correction coefficient stored in the correction value storing section 26.

In the above description, the medical device 1 of the present embodiment shown in FIG. 2 is used, but a medical device 101 of a first modified example of the present embodiment shown in FIG. 9 may be used, in which an endoscope apparatus 102 includes an advancement/retraction amount detection section 18 (which will be explained later), and an insertion assist apparatus 103 calculates a protruded amount D, so that the distal end-position calculation section 23 calculates a treatment instrument distal end position B1 based on the protruded amount D.

Alternatively, a medical device 201 of a second modified example of the present embodiment shown in FIG. 10 may be used, in which an endoscope apparatus 202 includes the treatment instrument 4 having the position detection sensor 19A thereon, and an insertion assist apparatus 203 calculates a protruded amount D, so that the distal end-position calculation section 23 calculates a treatment instrument distal end position B1 based on the protruded amount D.

The medical device 1 allows a surgeon to achieve precise examination or treatment because the position of the distal end portion B1 of the treatment instrument 4 can be corrected even when the reference point A1 moves.

Second Embodiment

Figure 11:
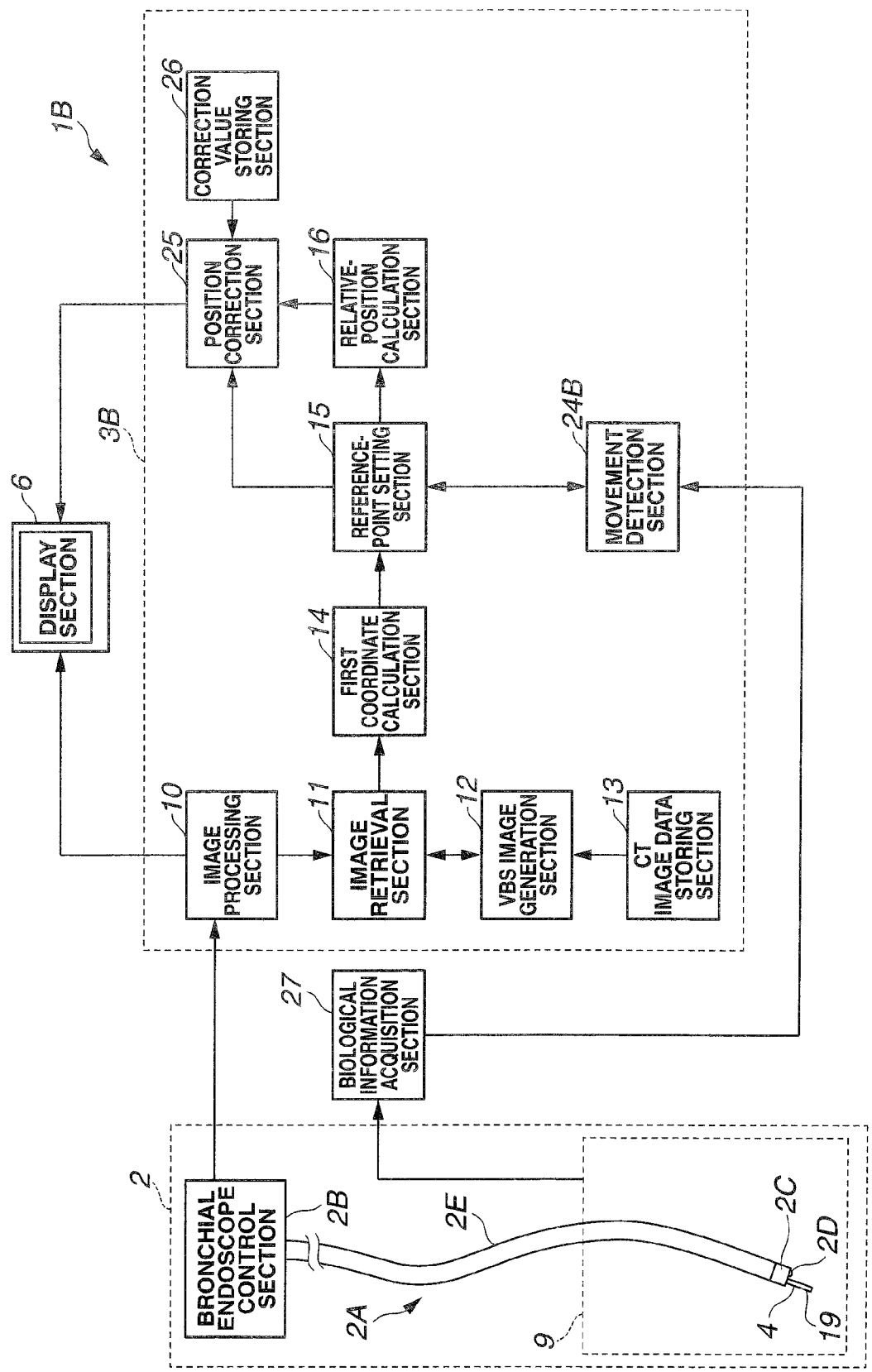
FIG. 11 is a configuration view showing a configuration of a medical device according to a second embodiment.
Figure 12:
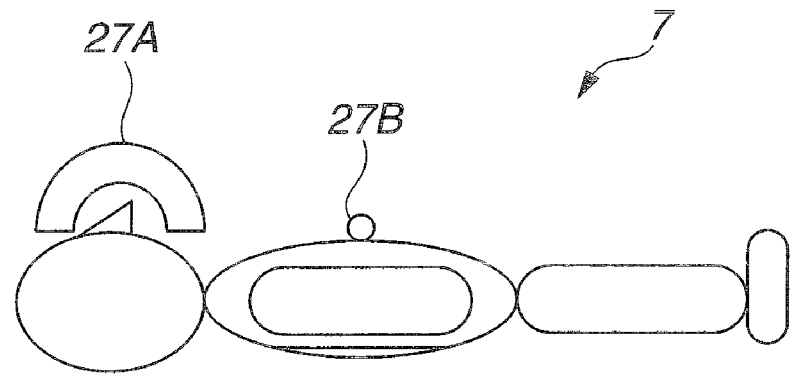
FIG. 12 is an illustrative view of a use form of the medical device according to a second embodiment.
Figure 13:
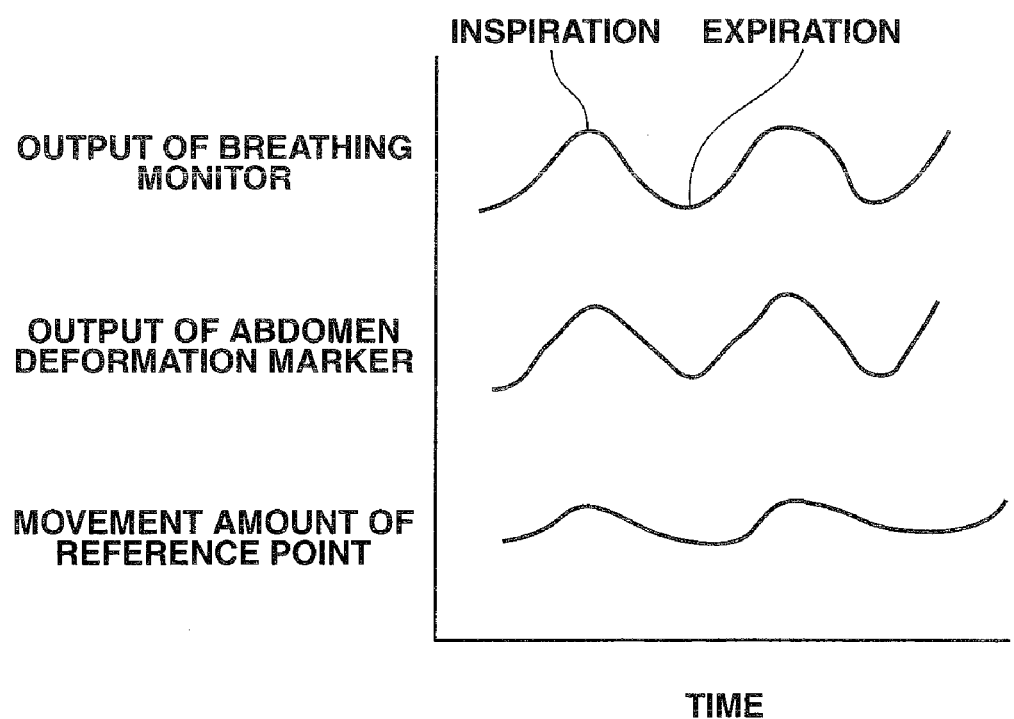
FIG. 13 is a graph illustrating a measurement example by a biological information acquisition section of the medical device according to the second embodiment.
Figure 14:
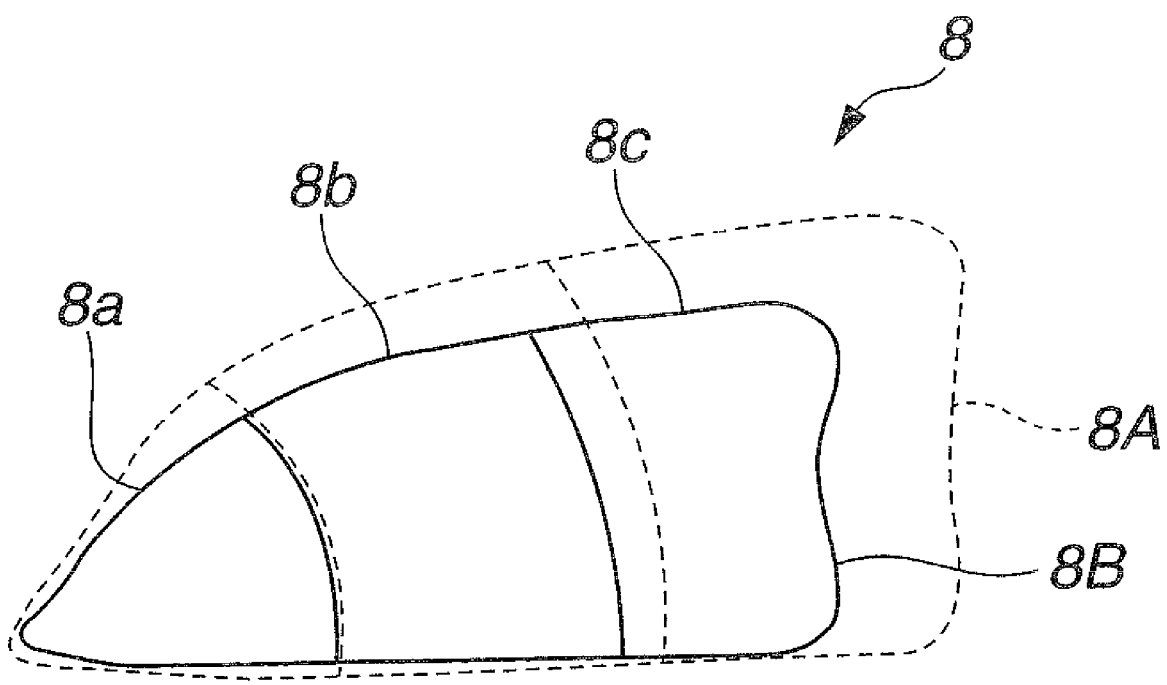
FIG. 14 is an illustrative view of displacement of a lung caused by breathing.
Figure 15:
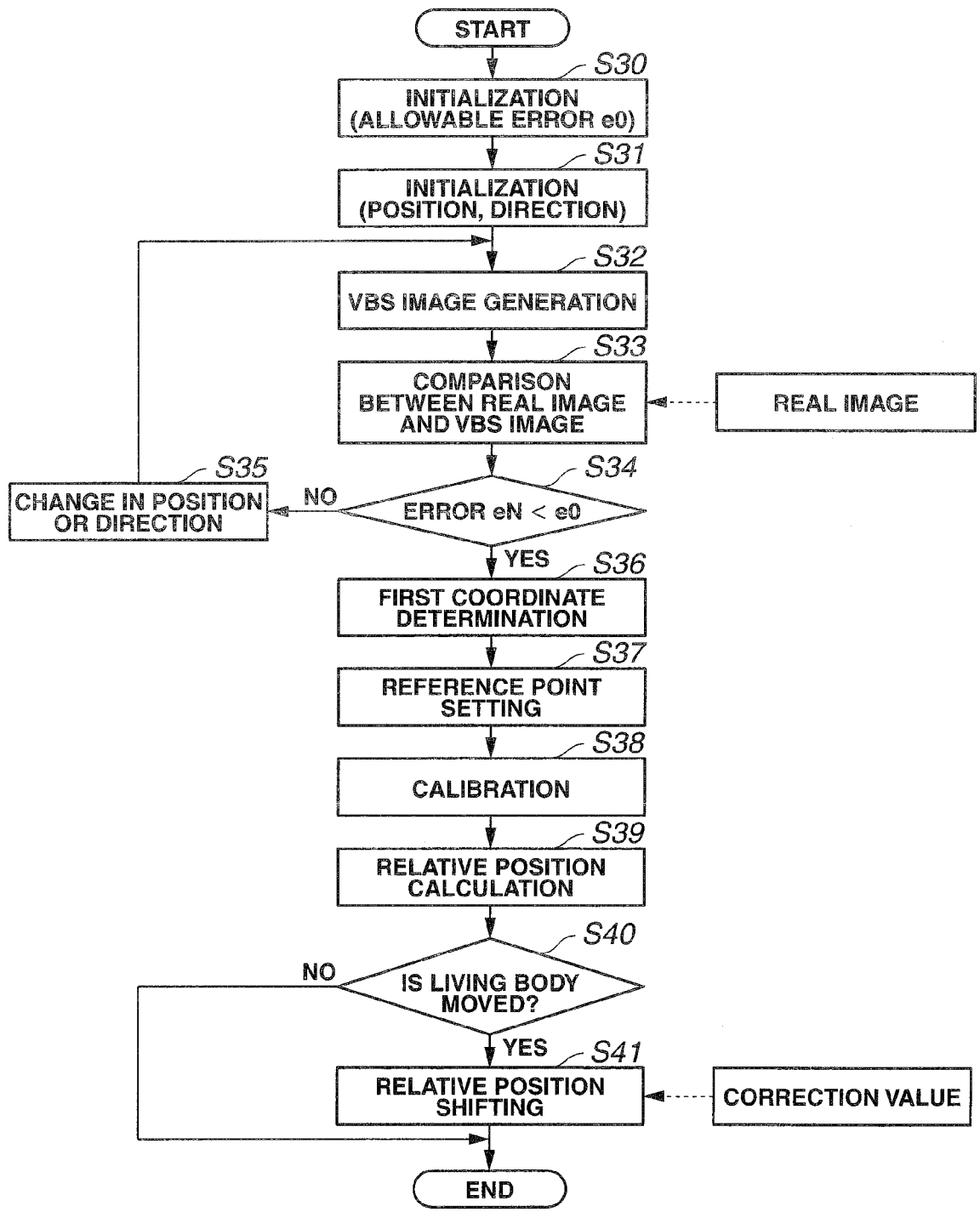
FIG. 15 is an illustrative view of deformation volume of lungs caused by breathing of a patient.

Now, with reference to the drawings, a medical device 1B of a second embodiment according to the present invention will be explained below. The medical device 1B is similar to the medical device 1, and the same components thereof are denoted by the same reference numerals, which will not be explained below. FIG. 11 is a configuration view showing a configuration of the medical device 1B of the second embodiment according to the present invention; FIG. 12 is an illustrative view of a use form of the medical device 1B; FIG. 13 is a graph illustrating a measurement example by a biological information acquisition section of the medical device of the present embodiment; FIG. 14 is an illustrative view of displacement of a lung caused by breathing; and FIG. 15 is a flowchart illustrating a process flow of an insertion assist apparatus of the medical device of the present embodiment. In FIG. 11, a detection section, a position detection sensor, and the like for measuring a protruded amount D of the treatment instrument 4 are not shown.

As shown in FIGS. 11 and 12, the medical device 1B includes: a breathing monitor 27A and an abdomen displacement monitor 27B, both of which constitute a biological information acquisition section 27 configured to acquire biological information; and a movement detection section 24B configured to detect a movement of a subject, in other words, a movement of the lung 8 or the bronchus 9. As shown in FIG. 12, the breathing monitor 27A is placed on a part near the mouth or nose of the patient 7 to detect a state of breathing of the patient 7, and the abdomen displacement monitor 27B is also placed on the abdomen of the patient 7 to detect a state of breathing of the patient 7.

As shown in FIG. 13, the breathing monitor 27A and the abdomen displacement monitor 27B individually output a detection of a state of breathing of the patient 7, that is, a detection of a deformation of the bronchus 9 in real time or as needed. A normal deformation volume of the bronchus 9 caused by the breathing of the patient 7 can be calculated in advance. This allows the movement detection section 24B to detect a movement of the bronchus 9 in real time or as needed. The medical device 1B may include a breathing information detection section formed with either one of the breathing monitor 27A and the abdomen displacement monitor 27B as the biological information acquisition section 27.

As shown in FIG. 14, a deformation volume of the lung 8 caused by the breathing of the patient 7 varies depending on a region of the lung 8. Generally, the areas 8c near the diaphragm deform more than the areas 8a far from the diaphragm. Of course, the bronchus 9 deforms similarly to the lung 8. Thus, preferably, the medical device 1B generates and stores correction value data or a formula for correction in the correction value storing section 26 in advance, so that a relative position of the distal end portion B1 of the treatment instrument 4 to the reference point A1 can be corrected using the data or formula depending on the position in the bronchus 9 where the treatment instrument 4 is inserted. The correction data depending on the position of the bronchus 9 may include a correction value for a part of the bronchus 9 in each of blocks of the lung 8 divided into appropriate areas, or include a correction value that is calculated in every correction process using a formula for correction based on a coordinate of the distal end portion B1 of the treatment instrument 4.

The above description corresponds to Step S40 and Step S41 in the flowchart illustrating a process flow of an insertion assist apparatus 3B shown in FIG. 15.

The medical device 1B includes: a movement detection section 24B configured to detect a movement of the bronchus 9 of a subject; and a position correction section 25 configured to correct a relative position of the distal end portion B1 of the treatment instrument 4 to the reference point A1 depending on a state of the breathing of the patient 7 and the position of a target site. Thus, the medical device 1B provides an advantage, in addition to the effects provided by the medical device 1 and the like, that a more precise examination or treatment can be performed by a surgeon.

Modified Example of Second Embodiment

Now, with reference to the drawings, a medical device 1C of a modified example of the second embodiment according to the present invention will be explained below. The medical device 1C is similar to the medical device 1, and the same components thereof are denoted by the same reference numerals, which will not be explained below.

The medical device 1B of the second embodiment has a breathing monitor and an abdomen displacement monitor as the biological information acquisition section 27. To the contrary, the medical device 1C of the present modified example uses an endoscopic image as the biological information acquisition section 27, which will be explained below with FIGS. 16A to 18B. FIGS. 16A to 18B are illustrative views of a biological information acquisition section.

Figure 16A:
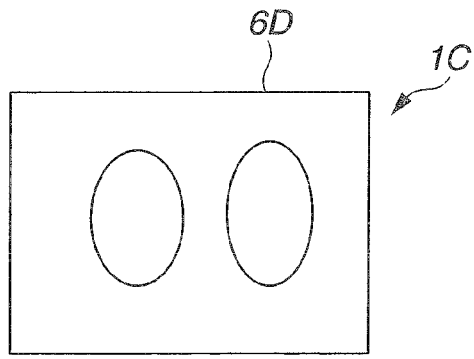
FIGS. 16A and 16B are illustrative views of a biological information acquisition section.
Figure 16B:
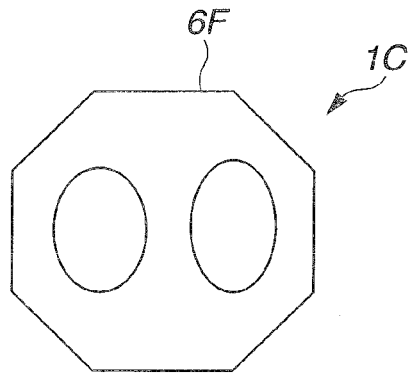

FIG. 16A shows a virtual endoscopic image 6D, while FIG. 16B shows a real image 6F. The medical device 1C is an example in which the similarity between the virtual endoscopic image 6D and the real image 6F is obtained, and a difference in the biological information between the images is detected based on the similarity value.

Figure 17A:
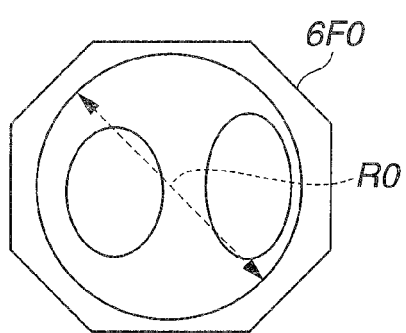
FIGS. 17A and 17B are illustrative views of a biological information acquisition section.
Figure 17B:
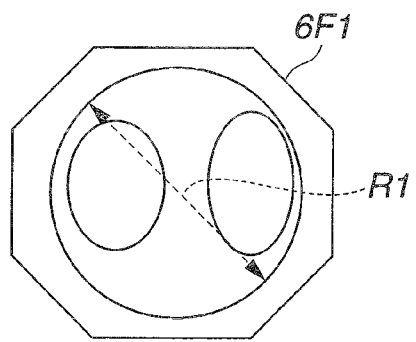

FIG. 17A shows a real image 6F0 in the past, while FIG. 17B shows a real image 6F at present. The medical device 1C is an example in which the difference in biological information between the images is detected based on a temporal change shown in the real image. For example, a difference in the shape of the actual bronchus 9 is calculated based on the difference in the diameter R (R1−R0) of the tube wall between the real images.

Figure 18A:
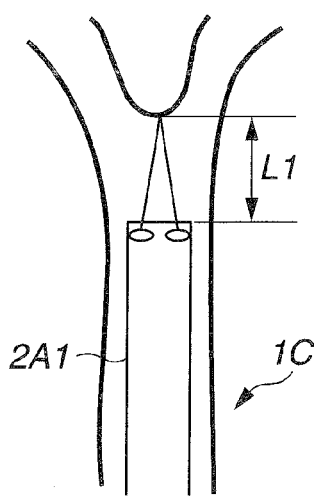
FIGS. 18A and 18B are illustrative views of a biological information acquisition section.
Figure 18B:
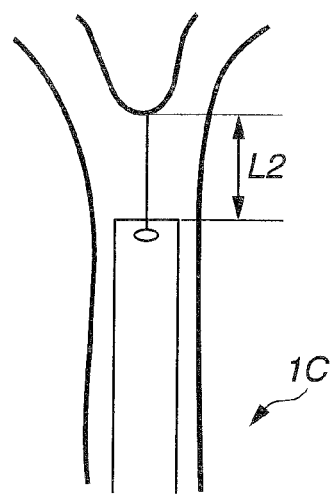

FIG. 18A shows a state where a distance L1 between the distal end portion 2C to a branch is measured with a stereo endoscope apparatus 21. While FIG. 18B shows a state where a distance L2 between the distal end portion to a branch of the virtual endoscope is measured based on a three-dimensional virtual endoscopic data. An example is shown in which the difference in biological information is detected using the measured distance L1 and the distance L2 in a CT coordinate system.

The medical device 1C provides an advantage, in addition to the effects provided by the medical device 1B and the like, that a more precise examination or treatment can be performed by a surgeon.

Third Embodiment

Now, with reference to the drawings, a medical device 1D of a third embodiment according to the present invention will be explained below. The medical device 1D is similar to the medical device 1, and the same components thereof are denoted by the same reference numerals, which will not be explained below.

The medical device 1D is provided with, as already explained above, three-dimensional image data of the bronchus 9 of the patient 7 that is obtained by a CT apparatus in advance. Here, simple representations of a state of a branch of a tube cavity, a length to each branch, and the like based on three-dimensional image data of the bronchus 9 are important to increase the process speed of the medical device 1D. Thus, the medical device 1D uses the so-called concept of "centerline and volume." The centerline is the line connecting the points of the center of gravity of the planes of a tube cavity that are orthogonal to the longitudinal direction, while the volume is the information showing the position of a tube wall in the tube cavity. The centerline is a piece of information in the longitudinal direction of a tube cavity, and may be the information such as a central line connecting the points of the center of the planes of a tube cavity that are orthogonal to the longitudinal direction.

Then, the medical device 1D includes the position detection sensor 19A near the distal end portion 2C of the treatment instrument 4 to measure the position of the distal end portion 2C in real time. However, the position detection sensor 19A detects a position in an endoscope coordinate system based on the endoscope apparatus 2, which is different from a CT coordinate system by which a virtual endoscopic image is represented. As a result, when transformed into a CT coordinate system, the position of the distal end portion 2C or treatment instrument 4 inserted in the bronchus 9 is sometimes represented at a position out of a tube cavity of the bronchus 9 that cannot exist. The reference point A1 of the distal end portion 2C which ought to be at a position near the center of the cross section in the longitudinal direction of a tube cavity of the bronchus 9 is sometimes represented at a position far from the center.

Thus, the medical device 1D includes a position correction section 25 configured to correct a position of the distal end portion 2C for example that is measured by an endoscope coordinate system and transformed into a CT coordinate system.

Figure 19A:
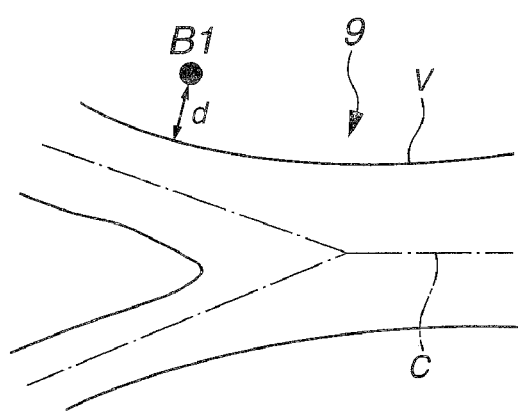
FIGS. 19A and 19B are illustrative views of a correction by a medical device.
Figure 19B:
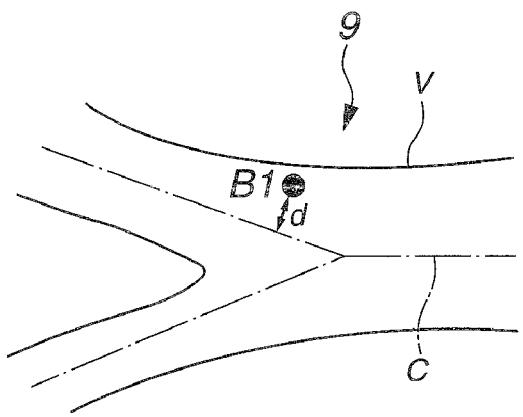

FIGS. 19A to 20C are illustrative views of a correction by the medical device 1D. As shown in FIG. 19A, the position correction section 25 of the medical device 1D corrects a position of the distal end portion B1 for example, when a position of the distal end portion B1 detected by the position detection sensor 19A is separated from a wall surface V by a predetermined distance d according to volume information, or as shown in FIG. 19B, separated from the centerline C by a predetermined distance d. The correction of the position of the distal end portion B1 means a change of the position in an endoscope coordinate system into a position in a CT coordinate system.

Figure 20A:
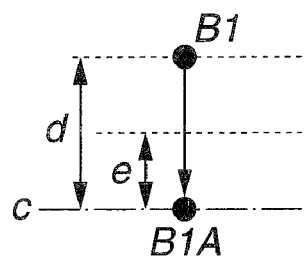
FIGS. 20A to 20C are illustrative views of a correction method by a position correction section.
Figure 20B:
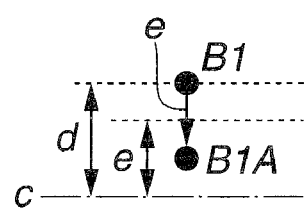
Figure 20C:
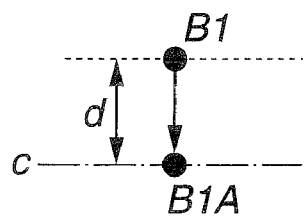

As shown in FIGS. 20A to 20C, the correction by the position correction section 25 may be performed using various correction methods. That is, in FIG. 20A, a correction method is shown in which the distal end portion B1 separated from a centerline C or wall surface V (hereinafter, referred to as "centerline and the like") by a predetermined distance e or more d is moved toward the centerline and the like by a distance d to a position B1A. The distal end portion B1 separated from a centerline and the like by less than a predetermined distance e is not corrected.

In FIG. 20B, a correction method is shown in which the distal end portion B1 separated from a centerline and the like by a predetermined distance e or more d is moved toward the centerline and the like by the predetermined distance e to a position B1A.

In FIG. 20C, a correction method is shown in which the distal end portion B1 separated from a centerline C and the like by a distance d is moved toward the centerline and the like by the distance d to a position B1A.

The selection of volume information or centerline C information to be used as a reference for setting of the predetermined distance e and performing a correction is preferably made based on the diameter of a tube cavity of the bronchus 9 in which the distal end portion B1 is inserted. That is, preferably, volume information is used for a tube cavity having a larger diameter with a predetermined distance e that is set to be relatively large, and centerline information is used for a tube cavity having a smaller diameter with a predetermined distance e that is set to be relatively small. In a tube cavity with a large diameter, a correction process is repeated more times for a smaller predetermined distance e, while in a tube cavity with a small diameter, a correction process is repeated more times for a larger predetermined distance e.

Figure 21:
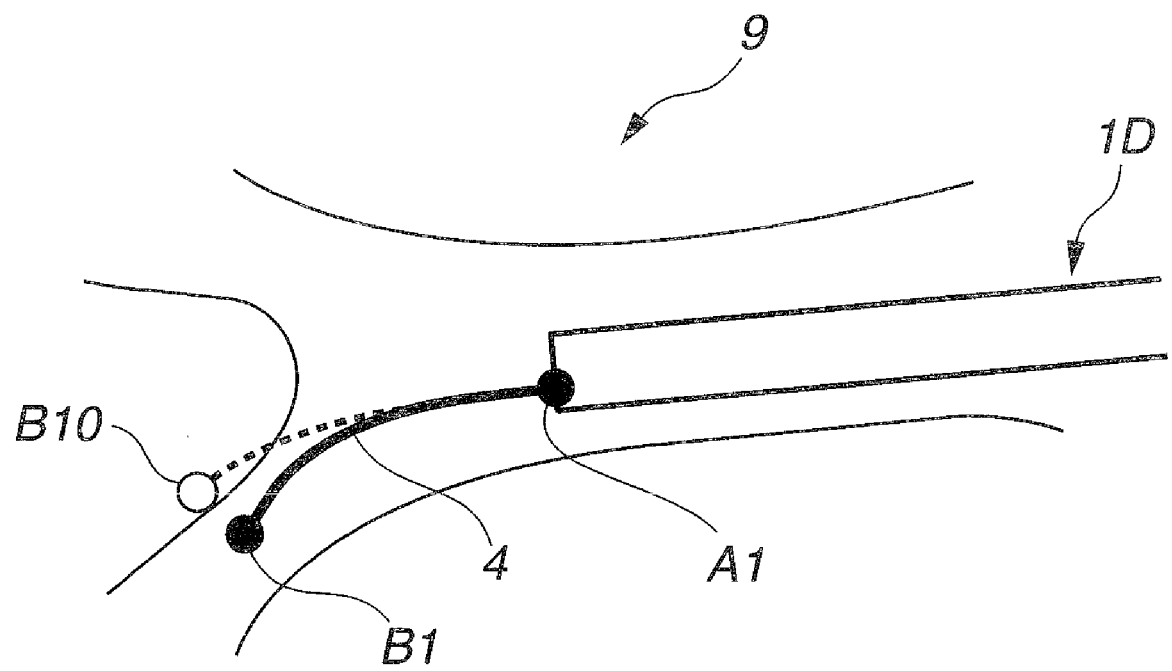
FIG. 21 is an illustrative view of a correction of a position of a treatment instrument.

A positional correction of a treatment instrument with the methods shown in FIGS. 19A to 20C enables the initial position of the treatment instrument shown by B10 to be corrected to the position shown by B1 as shown in FIG. 21.

As described above, without changing the biological information based on medical images such as CT, that is, CT coordinate system information, by correcting a coordinate system acquired by the position detection sensor 19 relative to the CT coordinate, a treatment instrument can be correctly represented as being in a living body, specifically in a bronchus tube cavity.

Fourth Embodiment

Now, with reference to the drawings, a medical device 1E according to the present invention will be explained below. The medical device 1D is similar to the medical device 1, and the same components thereof are denoted by the same reference numerals, which will not be explained below.

The difference between a representation in a CT coordinate space based on three-dimensional data and a representation in a real space based on an endoscope coordinate system is sometimes caused by a deformation of the elastic bronchus 9A due to a contact with the treatment instrument 4 or the like, in addition to the above described deformation of the lung 8 due to breathing of the patient 7.

Figure 22A:
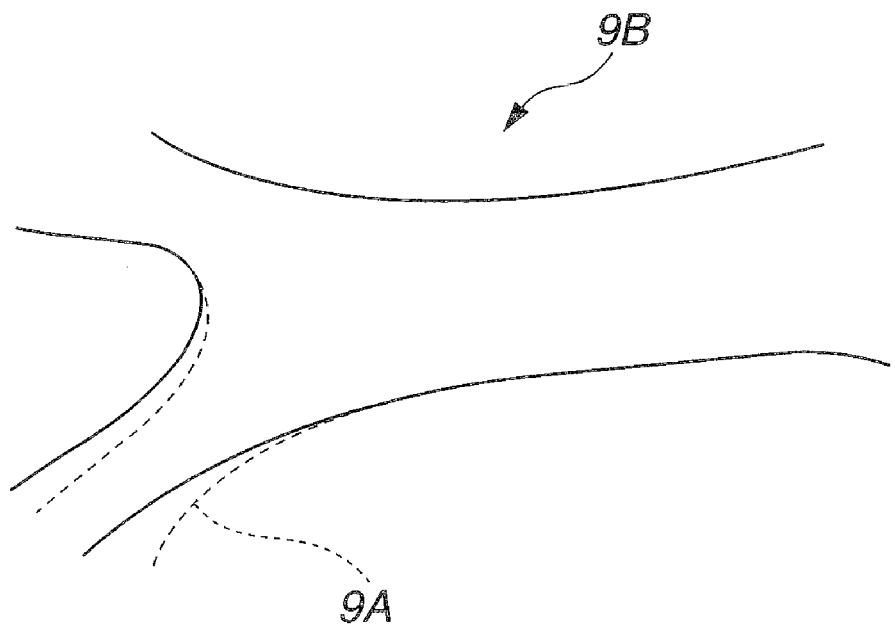
FIGS. 22A and 22B are illustrative views of a method for correcting a position of a distal end portion of a fourth embodiment.
Figure 22B:
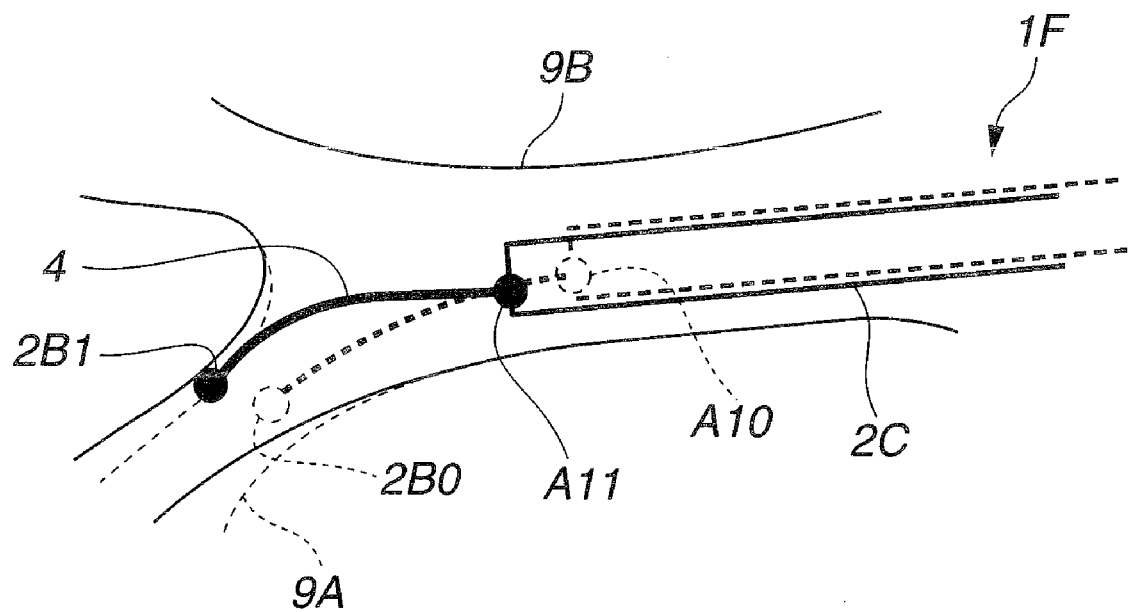

FIG. 22A is an illustrative view of a state of the bronchus 9A when a CT image thereof is picked up, and FIG. 22B is an illustrative view of a state where the bronchus is deformed due to a contact with the treatment instrument 4 or the like.

As shown in FIG. 22B, the position correction section 25 corrects the position 2B0 of the distal end portion 2C to the position 2B1. In the correction, a different correction value R is selected and used from the correction value storing section 26 depending on an area of the lung 8 where the distal end portion 2C is located.

As shown in FIG. 22B, in the medical device 1D, when the position of the treatment instrument 4 is changed due to the operation of the treatment instrument 4, the position correction section 25 further selects a different correction value corresponding to an area of the lung 8 from the correction value storing section 26 according to an amount of advancement/retraction of the treatment instrument 4, and uses the correction value. Specifically, an amount of change of the bronchus 9A is calculated using the positional change (from A10 to A11) of the reference point detected by the second position detection sensor 19A incorporated in the distal end portion 2C, and the distal end position B1 of the treatment instrument 4 is corrected based on the amount of change of the bronchus 9A. That is, a correction value corresponding to a position in the tube cavity the existence of which is predicted by the medical device is read from the correction value storing section 26, and a correction is performed based on the correction value.

Now, the advancement/retraction amount detection section 18 will be explained below. As shown in FIG. 1, the treatment instrument 4 is inserted into the channel 2F1 from the treatment instrument insertion port 2F2 on the proximal end side of the endoscope 2A, and is protruded from the treatment instrument port 2F of the distal end portion 2C. The length of the channel 2F1 is known. Thus, the distal end-position calculation section 23 of the medical device 1E detects the length of the treatment instrument 4 inserted from the treatment instrument insertion port 2F2, that is, an amount of advancement/retraction of the treatment instrument 4 in the channel of the medical device 1E with the advancement/retraction amount detection section 18, so as to calculate the distal end portion position of the treatment instrument 4 and a distance D of the treatment instrument 4 protruded from the treatment instrument port 2F.

Figure 23A:
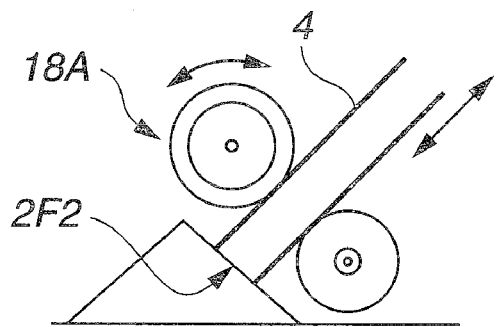
FIGS. 23A to 23C are illustrative views of specific examples of an advancement/retraction amount detection section of the fourth embodiment.
Figure 23B:
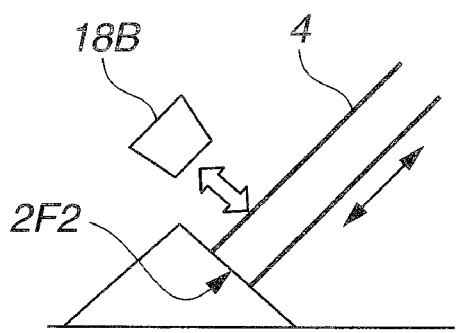
Figure 23C:
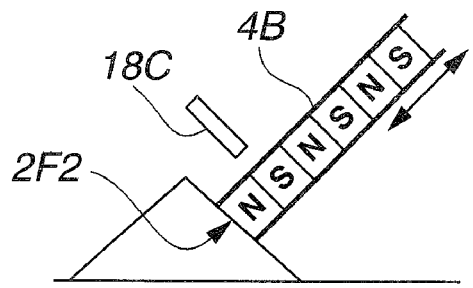

FIGS. 23A to 23C are illustrative views of specific examples of the advancement/retraction amount detection section 18. FIG. 23A shows an encoder 18A as one example of the advancement/retraction amount detection section 18 that is arranged near the treatment instrument insertion port 2F2; FIG. 23B shows an optical detector 18B for the detection; and FIG. 23C shows a magnetic sensor 18C for the detection.

The encoder 18A includes a rotary section on the treatment instrument 4 that rotates in response to an advancement/retraction of the treatment instrument, so as to detect the amount of advancement/retraction. The optical detector 18B detects a movement, that is, an amount of advancement/retraction of the treatment instrument 4 by using infrared ray or laser. The magnetic sensor 18C detects a movement, that is, an amount of advancement/retraction of the treatment instrument 4 based on a magnetic scale arranged at a treatment instrument 4B.

FIGS. 23A to 23C show examples in which sensors as the advancement/retraction amount detection section 18 are arranged at the treatment instrument insertion port 2F2, but the sensors may be arranged at the main body of the endoscope 2A such as the operation section thereof, or at the treatment instrument 4.

The medical device 1D enables a more accurate correction, and provides an advantage, in addition to the effects provided by the medical device 1 and the like, that a more precise examination or treatment can be performed by a surgeon.

Fifth Embodiment

Now, with reference to the drawings, a medical device 1F of a fifth embodiment according to the present invention will be explained below. The medical device 1F is similar to the medical device 1, and the same components thereof are denoted by the same reference numerals, which will not be explained below.

The above described medical device 1 of the first embodiment and the like use a correction method with the position correction section 25 in which an endoscope coordinate system is transformed to a CT coordinate system. To the contrary, in a correction method used in the medical device 1F of the fifth embodiment, a CT coordinate system is transformed to an endoscope coordinate system.

Figure 24A:
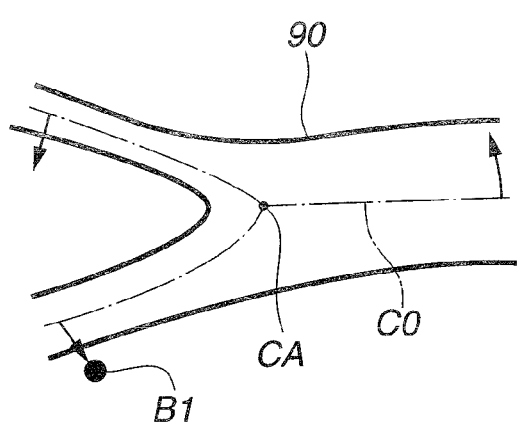
FIGS. 24A and 24B are illustrative views of a method for correcting a position by a medical device of a modified example of a fifth embodiment.
Figure 24B:
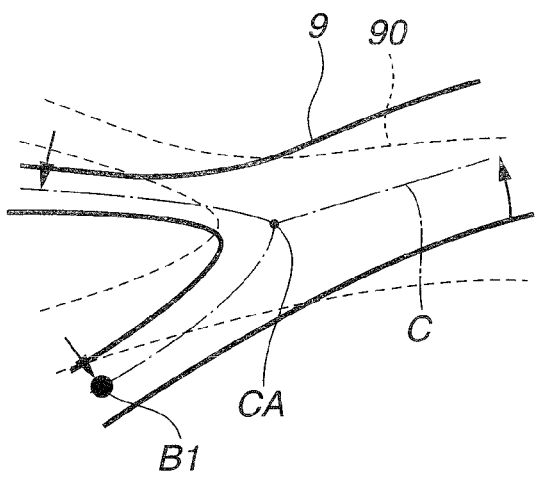

That is, as shown in FIGS. 24A and 24B, in the medical device 1F (not shown), on the assumption that the distal end portion 2C is at the position Sn based on the position detection sensor 19B at a time Tn, the tube cavity represented in a CT coordinate system with a prior branch as a center point is rotationally moved so that the centerline C passes through the position Sn.

The medical device 1F may perform the correction process not only by a rotational movement, but by scaling up/down or translational movement.

The medical device 1F provides the same operational effects as those of the medical device 1.

In the above description, the endoscope is the endoscope having the elongated insertion section 2E, but a medical device of the present invention may be a capsule endoscope having an image pickup section 2D that is able to pick up an image of tube cavity in the body of a patient 7, which also provides the same operational effects as those of the endoscope apparatus 2 having the elongated insertion section 2E.

A medical device of the present invention includes: an insertion section that is insertable through a bronchus of a subject, has a channel formed therein through which a medical instrument for examination or treatment based on a reference point in the bronchus is insertable, and has an opening of the channel and an image pickup section that is able to pick up an image of the bronchus at a distal end portion thereof; a virtual endoscopic image generation section configured to generate a virtual endoscopic image of the bronchus from a plurality of different sight line positions using three-dimensional image data of the bronchus that is obtained in advance, and generate a more highly similar virtual endoscopic image based on the information of the most highly similar virtual endoscopic image that is retrieved by an image retrieval section configured to retrieve the virtual endoscopic image highly similar to the endoscopic image of the bronchus picked up by the image pickup section; a reference-point setting section configured to set a reference point based on the line-of-sight positions of the more highly similar virtual endoscopic image; a position detection section configured to detect a position of the medical instrument; a relative-position calculation section configured to calculate a relative position of the medical instrument to the reference point based on the position of the medical instrument and the reference point; a movement detection section configured to detect a movement of the reference point or the subject; and a position correction section configured to correct the relative position in response to the movement of the reference point or the subject detected by the movement detection section.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical device, comprising:
    an endoscope with an insertion section that is insertable through a tube cavity in a subject, the insertion section having a channel formed therein, the insertion section having an opening of the channel at a distal end portion of the insertion section;
    an image pickup section that is able to pick up an image of the tube cavity in the subject, the image pickup section being disposed at the distal end portion of the insertion section;
    a medical instrument for examination or treatment in the tube cavity, the medical instrument being insertable through the channel, the medical instrument being configured to protrude from the distal end portion of the insertion section through the opening;
    a virtual endoscopic image generation section configured to generate a virtual endoscopic image of the tube cavity from a plurality of different line-of-sight positions using three-dimensional image data of the tube cavity that is obtained in advance;
    an image retrieval section configured to retrieve the virtual endoscopic image highly similar to the endoscopic image of the tube cavity in a body picked up by the image pickup section;
    a reference-point setting section configured to set a reference point based on a line-of-sight position of the highly similar virtual endoscopic image, wherein the reference point is positioned at the opening;
    a relative-position calculation section configured to calculate a relative position of the medical instrument to the reference point;
    a movement detection section configured to detect a movement of the reference point or the subject; and
    a position correction section configured to correct the relative position in response to the movement of the reference point or the subject detected by the movement detection section.

2. The medical device according to claim 1, wherein
    the virtual endoscopic image generation section generates a more highly similar virtual endoscopic image based on the information from the image retrieval section, and
    the reference-point setting section sets the reference point based on a line-of-sight position of the more highly similar virtual endoscopic image.

3. The medical device according to claim 1, wherein
    the image retrieval section retrieves the most highly similar virtual endoscopic image among the plurality of the virtual endoscopic images generated by the virtual endoscopic image generation section in advance,
    the virtual endoscopic image generation section generates a still more highly similar virtual endoscopic image based on the information of the most highly similar virtual endoscopic image retrieved by the image retrieval section, and
    the reference-point setting section sets the reference point based on a line-of-sight position of the still more highly similar virtual endoscopic image.

4. The medical device according to claim 1, further comprising:
    a position detection section configured to detect a position of the medical instrument; and wherein
    the relative position calculation section calculates the relative position based on the position of the medical instrument and the reference point.

5. The medical device according to claim 4, wherein
    the relative position calculation section calculates the relative position based on the position of the medical instrument and a new reference point obtained using the movement amount of the reference point.

6. The medical device according to claim 1, wherein insertion of the medical instrument through the channel comprises movement of the medical instrument through the channel from at least a first position to at least a second position.

* * * * *